United States Patent [19]
Attig et al.

[11] Patent Number: 4,736,054
[45] Date of Patent: Apr. 5, 1988

[54] AMMOXIDATION OF PARAFFINS TO ACRYLONITRILE IN THE PRESENCE OF ZEOLITE CATALYSTS

[75] Inventors: Thomas G. Attig, Aurora; Kenneth J. Kuruc, Garfield Hts.; Robert K. Grasselli, Chagrin Falls, all of Ohio

[73] Assignee: The Standard Oil Company, Cleveland, Ohio

[21] Appl. No.: 3,099

[22] Filed: Jan. 14, 1987

Related U.S. Application Data

[63] Continuation of Ser. No. 566,118, Dec. 27, 1983, abandoned.

[51] Int. Cl.$^4$ ............................................. C07C 120/14
[52] U.S. Cl. ................................................... 558/319
[58] Field of Search ......................................... 558/319

[56] References Cited

U.S. PATENT DOCUMENTS

| | | | |
|---|---|---|---|
| 3,412,134 | 11/1968 | Jones | 260/465 C |
| 3,652,638 | 3/1972 | Riegel et al. | 260/465.3 |
| 3,670,006 | 6/1972 | Taylor | 260/465.3 |
| 3,670,008 | 6/1972 | Taylor | 260/465.3 |
| 3,670,009 | 6/1972 | Taylor | 260/465.3 |
| 3,678,091 | 7/1972 | Reulet et al. | 260/465.3 |
| 3,700,585 | 10/1972 | Chen et al. | 208/111 |
| 3,702,886 | 11/1972 | Argomer et al. | 423/328 |
| 3,709,979 | 1/1973 | Chu | 423/328 |
| 3,746,737 | 7/1973 | Tullman | 260/465.3 |
| 3,770,614 | 11/1973 | Graven | 208/80 X |
| 3,816,506 | 6/1974 | Taylor | 260/465.3 |
| 3,832,449 | 8/1974 | Rosinski et al. | 423/328 |
| 3,833,638 | 9/1974 | Knox et al. | 260/465.3 |
| 3,925,447 | 12/1975 | Gelbein | 260/465 C |
| 3,948,758 | 4/1976 | Bonacci et al. | 208/92 |
| 4,060,590 | 11/1977 | Whittam et al. | 423/328 |
| 4,061,724 | 12/1977 | Grose et al. | 423/335 |
| 4,251,348 | 2/1981 | O'Rear et al. | 208/61 |
| 4,347,394 | 8/1982 | Detz et al. | 585/419 |
| 4,390,413 | 6/1983 | O'Rear et al. | 208/61 |

Primary Examiner—Joseph Paul Brust
Attorney, Agent, or Firm—M. F. Esposito; J. E. Miller; L. W. Evans

[57] ABSTRACT

The ammoxidation of n-butane to acrylonitrile and hydrogen cyanide by a process comprising reacting a gaseous mixture containing n-butane, ammonia and oxygen in the presence of a metal promoted highly siliceous zeolite catalyst, where the zeolite is one comprising ZSM-5, ZSM-5-type aluminosilicate zeolites, or aluminum-free ZSM-5-type zeolites, is disclosed.

13 Claims, No Drawings

AMMOXIDATION OF PARAFFINS TO ACRYLONITRILE IN THE PRESENCE OF ZEOLITE CATALYSTS

BACKGROUND OF THE INVENTION

This is a continuation of application Ser. No. 566,118 filed Dec. 27, 1983, now abandoned.

This invention relates to the ammoxidation of n-butane, isobutane and propane to acrylonitrile and hydrogen cyanide by a process utilizing a metal promoted highly siliceous zeolite catalyst.

The ammoxidation of lower aliphatic hydrocarbons to unsaturated nitriles, over various non-zeolite ammoxidation catalysts is known. For example, U.S. Pat. No. 3,833,638 discloses a method for the production of acrylonitrile or methacrylonitrile from propane or isobutane, ammonia and oxygen employing a catalyst containing cerium, molybdenum and bismuth or tellurium. Various other metal complex catalysts are disclosed in U.S. Pat. Nos. 3,670,006; 3,670,008; 3,670,009; 3,678,091; 3,746,737; and 3,816,506. Halogens are often used in this type of reaction to activate the alkane, such as in U.S. Pat. Nos. 3,833,638 and 3,652,638.

Zeolites are known substances and the use of zeolites other than ZSM-5-type zeolites in the preparation of various nitriles from unsaturated hydrocarbons is also known. For example, U.S. Pat. No. 3,412,134 discloses the preparation of unsaturated nitriles from corresponding unsaturated hydrocarbons and ammonia in the presence of a catalyst comprisng zeolites A, X or Y. Nitriles are produced by reacting unsaturated hydrocarbons or alkyl substituted aromatics and ammonia in the presnece of a supported metal oxide catalyst, wherein the support may be a zeolite in U.S. Pat. No. 3,925,447. Other reactions which are known to use ZSM-5-type zeolites are the processing of petroleum distillates so as to remove undesirable paraffins, as disclosed in U.S. Pat. Nos. 4,251,348 and 4,390,413, and the conversion of naphthas to benzene as disclosed in U.S. Pat. No. 4,347,394.

The catalysts of this invention are desirable because the low alumina content of the highly siliceous zeolites decreases catalyst acidity which is often detrimental to the ammoxidation reaction. Additionally, it is contemplated that the highly siliceous zeolites will render the catalysts thermally stable thereby prolonging the lift of the catalyst at elevated reaction temperatures. Furthermore, n-butane provides a significantly less expensive feedstock for producing acrylonitrile than currently used olefins.

SUMMARY OF THE INVENTION

According to this invention, n-butane, isobutane and propane undergo ammoxidation to crylonitrile and hydrogen cyanide by a process comprising contacting a gaseous mixture containing the paraffin, ammonia and oxygen with a metal-promoted highly siliceous zeolite catalyst, said catalyst having the folllowing general formula which is expressed in a ratio of weight percent:

$$M_a \text{ (zeolite)} \quad \text{(I)}$$

where

M is at least one of a Group VIII metal, Cu, Ag Zn, W, Mo, and Cr or oxides thereof;

zeolite is ZSM-5, ZSM-5-type aluminosilicate zeolites, or aluminum-free ZSM-5-type zeolites; and a is a number from 0.0001 to about 0.50.

DETAILED DESCRIPTION OF THE INVENTION

Catalyst

The catalytic compositions of this invention, as evidenced from formula I, comprise at least a two component material containing a metal component and a zeolite component.

The metal component is at least one metal from Group VII, Cu, Ag, Zn, W, Mo or Cr or an oxide of at least one of these materials. The preferred metal is platinum. The metal component may be included in the reaction mixture from which the zeolite is synthesized or the metal may be impregnated into the zeolite after it is formed by known methods in the art, as demonstrated in Example 1. The subscript "a" indicating the amount of metal (M) present in formula I is from about 0.0001 to 0.50, preferably from about 0.005 to 0.35 and most preferred from about 0.001 to 0.25 weight percent of the catalyst.

The zeolites of this invention have a high silica and a low alumina content, or contain no alumina at all. The silica to alumina ratio is greater than 12 and preferably is greater than 30. The highly siliceous nature of these zeolites permits thermal stability of the catalyst and a resulting prolonged catalyst life at elevated reaction temperatures. The low alumina content decreases catalyst acidity which is often detrimental to the ammoxidation reaction. Also characteristic of the zeolites of this invention is their medium pore size making them shape selective thus aiding in the prevention of coke formation precursors which may foul the catalyst and shorten its life. The effective pore aperture is in the range of about 5 to 6.5 Angstroms.

Suitable zeolites for the catalyst of the present invention include ZSM-5, ZSM-8, ZSM-11, ZSM-12, ZSM-21, and NU-1. Aluminum-free ZSM-5-type zeolites, such as silicalite are also useful in this invention. The preferred zeolite is ZSM-5.

ZSM-5 is described in U.S. Pat. Nos. 3,702,886 and 3,770,614; ZSM-8 is disclosed in U.S. Pat. No. 3,700,585; ZSM-11 is described U.S. Pat. No. 3,709,979; ZSM-12 is disclosed in U.S. Pat. No. 3,832,449; ZSM-21 is described in U.S. Pat. No. 3,984,758; NU-1 is described in U.S. Pat. No. 4,060,590; and silicalite is described in U.S. Pat. No. 4,061,724.

The use of the metal promoted zeolite catalysts of this invention eliminates the need for costly and potentially corrosive halide promoters, which have been used to activate alkanes in ammoxidation reactions.

The catalysts may be unsupported or supported. Suitable support materials include $SiO_2$, $Al_2O_3$ and $TiO_2$. A fixed or fluid bed operation may be utilized.

The catalyst compositions used herein are prepared by methods known in the art. One method is to mix proper proportions of the appropriate catalyst support with the zeolite in an aqueous mixture which is then dried. After grinding and screening the resulting solid to mesh particles, the metal in the form of an aqueous salt is added to the supported catalyst. The resulting impregnated material is dried, calcined and reduced with hydrogen.

Ammoxidation of n-Butane

The present invention is most conveniently carried out using n-butane as the reactant. However, it is also applicable to isobutane and propane.

The compositions of formula I are effective catalysts for the ammoxidation of n-butane to acrylonitrile. The reaction generally involves the contact of the gaseous reactant, ammonia and molecular oxygen at an elevated temperature in the presence of a catalytic amount of the composition of formula I.

The reaction is suitably conducted with about 0.5 to 10 moles of oxygen and about 0.5 to 5 moles of ammonia per mole of paraffin. It is preferred that the reaction proceed with about 1.0 to 4.0 moles of oxygen and about 1 to 2.5 moles of ammonia per mole of paraffin. Most preferred is a molar ratio of n-butane to ammonia to oxygen of 1 to 2 to 10. Molecular ozygen may be added as air.

The reaction is carried out at an elevated temperature such as 300° C. to 700° C., preferably 500° C. to 600° C. The ammoxidation reaction can be conducted in a fixed-bed or fluid-bed reactor using atmospheric, superatmospheric or subatmospheric pressure. The contact time of the reactants over the catalyst can vary and is dependent upon other reaction conditions of catalyst composition, feed composition, temperature, pressure and reactor design.

SPECIFIC EMBODIMENTS

Example 1

The catalyst used in the following example was prepared by adding ZSM-5 (21 g) to 40 percent silica sol (Nalco 2327) (13.2 g) and adding enough water to give a homogeneous mixture. The material was dried at 110° C. for 1 hour, then at 350° C. for 3 hours. The dried material was ground and screened to pass through 10–35 mesh screen. A solution of 0.05 g $Pt(NH_3)_4(NO_3)_2$ in 5 cc distilled water was added dropwise to the supported ZSM-5 (2.5 g). The resulting impregnated material was dried overnight at 110° C., then calcined to 550° C. for 4 hours. The catalyst was reduced with $H_2$ at 400° C. for 2 hours to yield a one percent Pt-ZSM-5 catalyst.

The ammoxidation of n-butane in the presence of ammonia and oxygen over a catalyst of formula I was conducted in a 5 cc microreactor with 10–35 mesh catalyst particles. A 1/2/10 mixture of n-butane/NH$_3$/air was passed over 5 cc of 80 percent (1 percent Pt-ZSM-5)-20 percent $SiO_2$ with a 3 second contact time at 550° C.

The conversion of n-butane was 43 percent with a product selectivity of 16 percent acrylonitrile, 3 percent HCN and 12 percent acetonitrile. Acrylonitrile and acetonitrile were analyzed by gas chromatography and HCN was analyzed by titration with 0.0141M $AgNO_3$ solution.

Although the invention has been described in terms of specific embodiments of a manner in which the invention may be practiced, this is by way of illustration only and the invention is not necessarily limited thereto since alternative embodiments and operating techniques will become apparent to those skilled in the art. Accordingly, modifications are contemplated which can be made without departing from the spirit of the described invention.

What is claimed is:

1. A process for the production of acrylonitrile by the ammoxidation of a reactant selected from the group consisting of n-butane, isobutane and propane, the process comprising contacting the gaseous reactant and ammonia with molecular oxygen at a temperature of 300° C. to 700° C. in the presence of a catalyst having the following formula:

$$M_a \text{ (zeolite)}$$

where

M is at least one of a Group VIII metal, Cu, Ag, Zn, W, Mo, or Cr or oxides thereof;

zeolite is an aluminosilicate zeolite having a silica to aluminia ratio greater than 12, or an aluminum-free zeolite wherein said zeolite has an effective pore aperture in the range of about 5 to 6.5 Angstroms; and a is a number from 0.0001 to about 0.50.

2. The process of claim 1 wherein the reactant is n-butane.

3. The process of claim 2 wherein M is platinum.

4. The process of claim 3 wherein zeolite is ZSM-5.

5. The process of claim 1 wherein zeolite is selected from a group consisting of ZSM-5, ZSM-8, ZSM-11, ZSM-12, ZSM-21 and NU-1.

6. The process of claim 1 wherein zeolite is silicalite.

7. The process of claim 1 wherein zeolite is a medium pore zeolite with a silica to alumina ratio greater than 12.

8. The process of claim 1 wherein the composition is used with a support.

9. The process of claim 5 wherein the support is a silica or an alumina.

10. The process of claim 4 wherein the subscript "a" in the composition formula is 0.001 to 0.25.

11. The process of claim 8 wherein the reactant is n-butane.

12. The process of claim 9 wherein the process is conducted at a temperature between 500° and 600° C.

13. The process of claim 11 wherein the molar ratio of n-butane to ammonia to oxygen is 1:2:10.

* * * * *